US00PP17787P2

(12) United States Plant Patent
White

(10) Patent No.: US PP17,787 P2
(45) Date of Patent: Jun. 5, 2007

(54) MINIATURE ROSE PLANT NAMED 'SAVAWORRY'

(50) Latin Name: *Rosa hybrida 'minima'*
Varietal Denomination: SAVaworry

(75) Inventor: Wendy White, Ipswich, MA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 0 days.

(21) Appl. No.: 11/319,351

(22) Filed: Dec. 28, 2005

(51) Int. Cl.
*A01H 5/00* (2006.01)

(52) U.S. Cl. ..... Plt./116

(58) Field of Classification Search ..... Plt./116
See application file for complete search history.

*Primary Examiner*—Kent Bell
*Assistant Examiner*—Annette H Para

(57) ABSTRACT

'SAVaworry' is a new and distinct variety of miniature rose plant, primarily identified by its semi-double, yellow flowers, edge with a shade of red, on a low growing plant, having many prickles. The flowers open to fully expose beautiful dark yellow stamens. The mature plant seems to always be in bloom form late spring to mid autumn. In low light conditions the plant will still produce flowers but it will loose any red coloration and be a lighter shade of yellow. 'SAVaworry' will grow and bloom well in the greenhouse or outdoors, in the ground or in containers. When grown in full sun, the bright colors provide a bright spot of decoration.

1 Drawing Sheet

CROSS REFERENCE

The rose in this same breeding program that most closely resembles this new invention is 'Poker Chip' (U.S. Plant Pat. No. 4,582, expired). The plant habits of these two plants are similar, both being well branched and growing twelve to fifteen inches tall and about two feet wide. Both have flowers of red and yellow. The diameter of the open bloom on 'Poker Chip' is 1¾ inches and on this new invention is 1½ inches. The differences are in petal count, 'Poker Chip' having twenty-five to thirty petals and the new invention having ten to fourteen, plus the coloration of those petals. The abaxial surface of both is yellow but the upper surface of 'Poker Chip' is primarily red while the upper surface of this new invention is yellow with red near the margins. The relationship between these two plants is with both the seed parent and pollen parent. The seed-parent of the seed-parents of both cultivars is 'Little Darling', U.S. Pat. No. 1,581, expired. The pollen parentage of both cultivars is also similar: The pollen parent of the new invention is 'SAVachild', (U.S. Plant Pat. No. 8,175), whose parentage is 'Yellow Jewel' (U.S. Plant Pat. No. 3,827) by 'MEIdanu' (not patented in the United States). The pollen parent of 'Poker Chip' is an unnamed seedling of the same cross, 'Yellow Jewel' by 'MEIdanu'.

Genus and species: *Rosa hybrida 'minima'*.

Varietal denomination: 'SAVaworry'.

BACKGROUND OF THE INVENTION

This present invention relates to a new and distinct variety of hardy, bush type plant of the miniature rose class. This variety was created by myself, Wendy R. White, under controlled conditions in a greenhouse in Rowley, Mass., by crossing as seed parent the variety known as 'MORsegold' (U.S. Plant Pat. No. 6,617) with the variety known as 'SAVachild' (U.S. Plant Pat. No. 8,175) as pollen parent.

The idyllic goals of this breeding program were to create unique miniature roses with the qualities of disease resistance, hardiness, exhibition, hybrid tea form blooms born in abundance from late spring to late fall, and fragrance. The cultivar chosen as seed parent is known for its above average disease resistance and quantity of bloom production on a vigorous plant. The cultivar chosen as pollen parent is known for its award winning, exhibition, hybrid tea form blooms on an award winning plant. Fragrance was not factored into this cross. The resulting new cultivar has the disease resistance and vigor of 'MORsegold' with the color-markings and flower form of 'SAVachild', and combines the colors of the two, being yellow like 'MORsegold' but with the red edges similar to 'SAVachild'. The new cultivar has a low and spreading plant habit similar to 'MORsegold' but carries its flowers on stronger stems as on 'SAVachild'. The new cultivar has fewer petals than either parent.

Asexual reproduction by cuttings of this new cultivar in Rowley, Mass., and Arroyo Grande, Calif., shows that all distinguishing characteristics of this rose continually come true to form.

BREIF SUMMARY OF THE INVENTION

The present invention relates to a new, distinct and low growing variety of hardy, bush type, miniature rose plant, which is primarily characterized by its semi-double, yellow flowers, edged with a shade of red when grown in full sun. The characteristics distinguishing it from all other varieties of which I am aware, besides the color of its semi-double flowers, are the size of those flowers and its low-growing, upright yet spreading plant habit. The variety is further characterized by:

- flowers that open fully to expose dark yellow stamens;
- numerous prickles, soft on the young growth, in a manner similar to its seed parent, 'MORsegold';
- medium to dark-green foliage;
- repeat to near continuous bloom from late spring to mid-fall;

flowers with little to no red coloring in low light levels;

a plant that grows and blooms satisfactorily both in the greenhouse and outdoors, providing decoration in the garden or containers.

BREIF DESCRIPTION OF THE DRAWING

The accompanying drawing is stems of 'SAVaworry' grown under plastic in Arroyo Grande, Calif., taken in natural daylight; the bottom image is a bud as sepals start to divide, taken in artificial lighting.

BOTANICAL DESCRIPTION OF THE PLANT

The following observations, measurements, values and comparisons describe four and five year old plants of *Rosa hybrida minima,* 'SAVaworry', of the miniature rose class, grown in 3, 8 and 10-inch plastic nursery containers in artificial soil mix in plastic covered houses in Arroyo Grande, Calif. Color references are made using The Royal Horticultural Society (London, England) Colour Chart, except where common terms of color are used.

FLOWERS

Blooming habit is rapid repeat bloom, always having at least a few flowers open on the mature plant. Most of the flowers are borne singly but also in small clusters of two to four.

Bud form is ovate with an acute apex. The diameter and height are nearly equal just before the sepals divide, between 6/16 and 7/16 inch wide and 7/16 to 8/16 inch high.

Sepals: The flower has five sepals. The color of their outer surfaces is a medium to dark green, nearest 144A suffused with near 137A, and with a basal area of near 144A. They may be flushed with a grayed-red. The inner surface is a medium shade of green between 191B, from the Greyed-Green Group, and 139C, with a tomentose covering.

The two outermost sepals have attenuate apices. Length varies from 25/32 inch to 1 3/32 inches, with the usual length of about 1 inch. Width at the widest point is usually 1/4 inch. The margin is ciliate. Their outer surface is pilose along the center, has stipitate glands in the basal area and may have glands randomly dotting the surface. There are one or two linear appendages, each tipped with a gland, along each margin. Sometimes these appendages appear as a single stipe, usually tipped with a gland. The foliar appendages have no hairs but may have a stipitate gland on them.

The two innermost sepals have acuminate apices. They are uniformly 15/16 inch long and 9/32 inch wide. Ciliata along the margins is heavier than on the outermost sepals and there is a heavier amount of hairs along the margins of the outer surface that decreases in amount towards the center. Margins are entire with no foliar appendages but may occasionally have a stipitate gland.

The one sepal in-between the inner and outer sepals has an attenuate apex and displays characteristics of both the inner and outer sepals, dividing down the center but with the basal area more like that of the inner sepals, having no stipitate glands. Length varies from 29/32 to 1 1/32 inches and width varies from 17/64 inch to 19/64 inch.

Sepals roll back ahead of the petals to near parallel with the stem with the tips recurved outward. When the petals drop the sepals return to a sixty-five to seventy-five degree angle with the stem, and remaining attached to the receptacle.

The receptacle is urceolate with a smooth, semi-glossy surface of a medium green, between 138A and 144A. The diameter is 5/16 inch and between 11/32 and 12/32 inch in height. Short, appressed, soft hairs are scattered on the surface. The surface on the top of the receptacle is glabrous with a diameter of 9/32 to 10/32 inch. The color is a light yellow-green, nearest 154C.

Peduncles are straight and strong. Anthocyanin coloring is absent. The surface is semi-glossy and a darker green than the receptacle, near 146A. The surface has very fine, short appressed hairs and a smattering of stipitate glands. The length of the peduncles varies from 7/8 inch to 1 1/16 inches but has been measured as short as 25/32 inch. The diameter is most often around 3/32 inch varying from 5/64 to 7/64 inch but having been measured as large as both 1/8 inch and 5/32 inch. There is usually a pair of three-leaflet leaves at the base but occasionally one is only a single-leaflet leaf.

Bloom size, when fully expanded, is usually around 1½ inches in diameter and about 1 inch deep. The upper and lower profiles of the open bloom are flattened convex. Petalage ranges from ten to fourteen petals with two to seven petaloides. Most often there are twelve or thirteen petals and two to four petaloides. Fragrance is slight.

Petals are thick with a velvety upper surface and satiny lower surface. The shape of the outer petals is broad spatulate, the intermediate petals are a broad, ovato-rotundate, and the innermost petals are narrower and obovate. The outer margins are arcuate. The six outermost petals have cuspidate apices and the remaining inner petals are emarginated. The bases of the petals are cuneate with the outer petals having broader cuneal bases. The width of the outermost petals ranges from 3/4 to 1 inch with the width of the individual petals on each flower varying by 1/32 or 1/16 inch. Their length ranges from 1 2/16 to 1 3/16 inches plus the apex extending an additional 1/16 inch. Petals are imbricated.

Color of the flowers is very dependent on the intensity of the light. These observations were taken from plants grown with exposure to direct sunlight, through greenhouse roofs that open. When the intensity of light is less, the colors become less intense, respectively, and the red coloration disappearing entirely at low light levels.

The petals during the first few days are a dark red-orange, nearest 34A, along the outer edges of the petals and becoming near 33A, Capsicum Red, as it blends in with the Straw Yellow, near 13C. The basal area is darker, Lemon Yellow, near 13B, and the point of attachment is near 13A. The reverse is near 13B and near 45A, from the Red Group, only on the margin. The point of attachment is near 13A. Any streaks on the reverse where the petals were exposed to the sun when the sepals first divided are nearest 45A.

When half blown, along the margins of the upper surface, the color lightens to a red between 52A and 53D. The yellow coloring remains unchanged. The reverse lightens a little, overall, to near 13D, with near 53C, Cardinal red, along the margins, a basal area near 13C and near 13B at the point of attachment.

As the blooms age, the upper surfaces are nearest 53D along the margin and becoming lighter, nearest 52B, Carmine, as it proceeds about one-third of the way into the petal, mixing with near 13D. The basal area is nearest 13C and the point of attachment is nearest 13B. The reverse is Aureolin, near 12D, with the basal area and point of attachment near 12B, and Crimson, nearest 52A, feathering in from the margin. Streaks on the reverse where the petals were exposed to the sun are nearest 52A.

Petaloides have the same color and texture as the petals. The width is variable, up to ½ inch at their widest point and ½ to 3/4 inch long when they are as only half a petal, lengthwise; or 3/32 to 5/32 inch wide and between 1/4 to 3/8 inch long when gnarled or occasionally epipetalous. Outer margins are either retuse or scalloped.

PLANT

The plant has good vigor and is uniformly branched. It will grow 10 to 14 inches tall and two feet or more wide. Lengths of the flowering stems range from 3⅛ inches to 9½ inches to the base of the peduncle. The usual lengths are 3⅛ inches when borne in clusters and about 8 inches when borne singly.

Foliage is pinnately compound, generally, with seven leaflets but occasionally with three or five. On the seven-leaflet leaves, the basal leaflets are not always opposite or one may be absent. There are generally four to seven leaves per stem. Spacing of the leaves on the main stalks generally increases progressing up the stem, from near ⅜ inch, 13⁄16 inch, ¾ inch, 1 inch and finally to 1½ inches. Spacing on primary laterals has been measured at 9⁄16 inch, 9⁄16 inch and ⅞ inch; and ½ inch, ⅞ inch and ¾ inch. Spacing on secondary laterals fluctuates randomly between ¾ and 1¼ inches. Spacing on candelabra stems, those originating from the base of the plant, are uniformly 1½ inches. The length of most mature leaves is 3³⁄₁₆ inches whether it has five or seven leaflets, from attachment to stem to tip of terminal leaflet. The seven-leaflet leaf may be as much as 3⁵⁄₁₆ inches long. The length of the three leaflet leaves varies between 2³⁄₁₆ and 3⅛ inches.

Leaflets are ovate with an acuminate apex and oval base. On a seven-leaflet leaf, the terminal leaflet measures between 11⁄16 and 13⁄16 inch wide and 1⁵⁄₁₆ inches long. On a five-leaflet leaf, the terminal leaflet measures from 11⁄16 to 13⁄16 inches wide and from 1¼ to 1⁹⁄₁₆ inches long. The margin has simple serration with a gland or stipitate gland at the tip of each serrate. The upper surface of the new foliage is glossy and mature foliage is semi-glossy; the under surface is matte. Both surfaces are glabrous. The main vein protrudes, almost entirely, on the underside of the leaflets and is recessed on the upper surface. Primary lateral veins only protrude some on the under surface and are also recessed on the upper surface. Secondary lateral veins are recessed on the abaxial surface only and are not visible on the upper surface.

Color of the new foliage is a dark green, nearest 137A, and flushed with near 181A from the Greyed-Red Group. Margins are also near 181A. The underside of the new foliage is a lighter yellowed-green, nearest 148B, and flushed lightly with near 181C. The anthocyanin coloring is absent form the older leaflets. The upper surface is a very dark yellowed-green, nearest 147A, and the under surface is nearest 147B.

Petioles appear a grayed-red, nearest 178A, and almost translucent, on the young growth. On mature leaves the color along the ridges is a deep yellowed-green, near 147A, with the grooves being considerably lighter, near 147D, and lightly flushed with reddish anthocyanin coloration. Along the ridges of the adaxial surface, there are a few stipitate glands, often paired, and a few hairs where the uppermost portion of the stipules is connected. There may be a few hairs in the groove. The abaxial surface is glabrous. The length of the petioles ranges from 18⁄32 to 23⁄32 inch on the seven leaflet-leaves and from 10⁄16 to 13⁄16 inch on five leaflet leaves. Diameter is 1⁄16 inch.

The rachis varies in length from 11⁄16 inch to 1³⁄₆₄ inches regardless of whether the leaf has five or seven leaflets. The most common length is slightly less than one inch. The color is the same as that of the petioles. The ridges of the rachis may have a few stipitate glands. The groove generally has a few hairs but with a tuft of hairs at the juncture of the petiolules, except those going to the basal leaflets, where there are generally only a few. There may be stipitate glands around the tufts. At the base of each petiolule, except those going to the basal leaflets, there are a few single hairs surrounding the base where it is attached to the rachis.

Petiolules are the same color as the petiole and rachis but without any anthocyanin coloring in the groove on mature leaves. The length to the terminal leaflet varies from 12⁄32 to 15⁄32 inch. The length to the first pair of leaflets below the terminal leaflet varies from 2⁄32 to 3⁄32 inch. The length the petiolules to the second set of leaflets varies from 3⁄64 to 4⁄64. The length of the petiolules to the basal leaflets is generally 5⁄64 inch. The ridges may have a few stipitate glands, may have one or a pair proceeding just down from the leaflets as if continuing from those on the serrates, may have many stipitate glands near evenly spaced, or may be glabrous. The grooves may have a few hairs or may be glabrous. The abaxial surface is glabrous.

Stipules recurve backward along the margin. Margins are slightly undulant and lined with near evenly spaced stipitate glands. The glands have a reddish, anthocyanin coloring. On the seven-leaflet leaves, the stipules are in even pairs attached to the base of the petiole for 6⁄16 to 7⁄16 inch and then angled out at about a forty-five degree angle from the petiole for an additional 3⁄32 to 4⁄32 inch. When there are fewer than seven leaflets on the leaf, the stipules are often attached in uneven pairs. Their length varies from 11⁄32 to ½ inch attached and angled out for an additional 2⁄16 to 3⁄16 inch. The length attached may vary by up to 3⁄32 inch in each pair. The color of the adaxial surface is between 144A and 138A. The reverse is darker and more yellowed, near 146B.

WOOD

The diameter of the main stems ranges from ¼ to 5⁄16 inch. The diameter of the primary laterals ranges from 6⁄32 to 7⁄32 inch and the diameter of the flowering stem ranges from 5⁄64 to 7⁄64 inch. The color of the young canes is near 146A and may be flushed with near 183A from the Greyed-Purple Group. The older canes are nearest 137B. There are numerous prickles and lenticels.

Lenticels start forming on the main canes and primarily laterals in the first year of growth. When young the color is nearest 166C and when old becomes near 177C, both from the Greyed-Orange Group.

Prickles mature to a color near that of the lenticels, near 166A or 166B. When young their color is near 187D at the base and having less Payne's gray, near 184C at the top, both colors are from the Greyed-Purple Group. At an intermediate age the color is a grayed-orange, between 165B and 166C. The form is most often slightly angled downward with a slight arcuate profile, and tapered evenly to a point. The quantity on the main stalk is about fifteen in three inches, increasing in quantity, upward and sunward. Quantity on primary laterals is around thirty-five in three inches, also with the highest quantity being upward and sunward. On secondary laterals the quantity varies from nine in two inches to fifteen in two inches or twenty-one in three inches. On flowering stems the quantity varies from seven to eleven in two and one-half inches of stem. The length on main canes and primary laterals varies from 5⁄32 and 6⁄32 inch; on secondary laterals, randomly, from 1⁄16 to ¼ inch; on flowering stems from 3⁄32 or 5⁄32 inch; and up to 5⁄16 inch on candelabra canes. The length of the linear base is near equal the length of the prickles on the candelabras and flowering stems, only. The length of the bases on other growth seems entirely random. The prickles on the rachis are nearest 159D, from the Orange-White Group, and nearly translucent.

Resistance to downey and powdery mildew is slightly above average. No rust has been observed. Resistance to aphids is good.

This new cultivar was tested hardy in the United States Department of Agriculture Hardiness Zones 5 through 10, which is comparable to the American Horticultural Society heat zones 10 through 4.

It is claimed:

1. A hardy, new and distinct variety of miniature rose plant is claimed, substantially as herein illustrated and described, having semi-double, yellow flowers normally edged with a shade of red when growth in full sun and borne on a low growing plant, having many prickles.

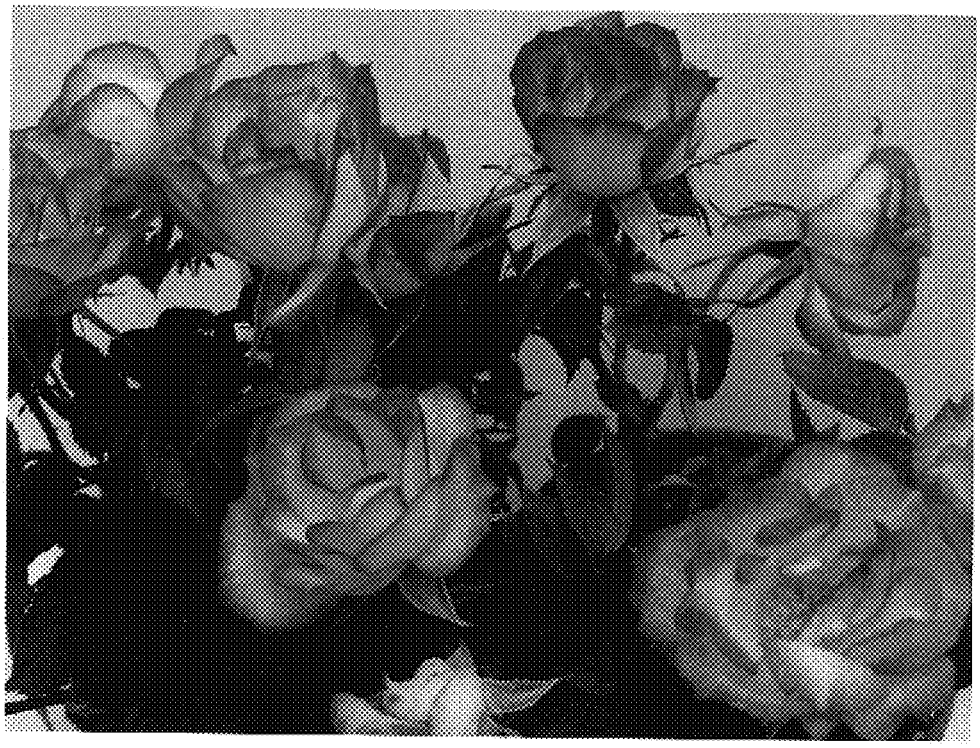
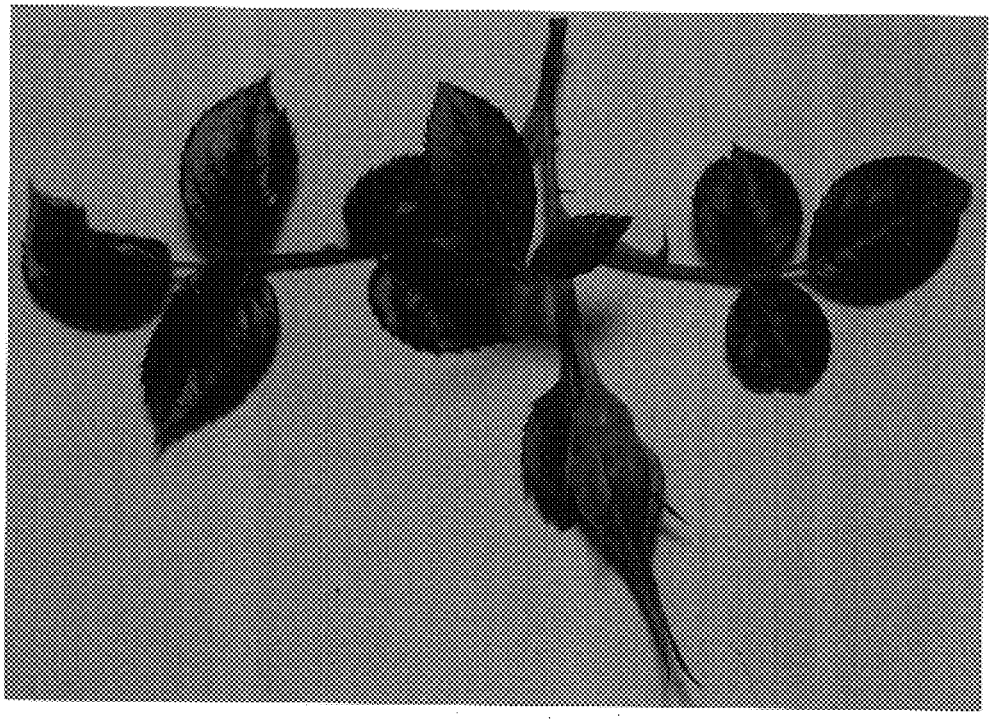

* * * * *